United States Patent [19]

Rody et al.

[11] 4,210,578

[45] Jul. 1, 1980

[54] 4-SILOXY DERIVATIVES OF POLYALKYLATED PIPERIDINES

[75] Inventors: Jean Rody, Basel, Switzerland; Gerd Greber, Bad Vöslau, Austria; Helmut Müller, Binningen, Switzerland

[73] Assignees: Ciba-Geigy Corporation, Ardsley, N.Y.; Sankyo Company, Limited, Tokyo, Japan

[21] Appl. No.: 961,836

[22] Filed: Nov. 17, 1978

Related U.S. Application Data

[63] Continuation of Ser. No. 853,664, Nov. 21, 1977, abandoned, which is a continuation-in-part of Ser. No. 687,824, May 19, 1976, abandoned.

[30] Foreign Application Priority Data

May 28, 1975 [GB] United Kingdom ............... 23351/75

[51] Int. Cl.$^2$ ................ C07D 211/46; C07D 401/12; C07D 401/14; C08K 5/54
[52] U.S. Cl. ..................... 260/45.8 N; 260/45.7 PH; 260/45.85 B; 526/265; 528/28; 528/38; 546/14
[58] Field of Search ............... 260/45.8 NP; 526/265; 528/28, 38; 546/14

[56] References Cited

U.S. PATENT DOCUMENTS

| | | | |
|---|---|---|---|
| 3,840,494 | 10/1974 | Murayama et al. | 260/45.8 N |
| 4,021,432 | 5/1977 | Holt et al. | 260/45.8 N |
| 4,075,165 | 2/1978 | Soma et al. | 260/45.8 N |
| 4,116,933 | 9/1978 | Ramey et al. | 260/45.8 N |
| 4,131,599 | 12/1978 | Brunetti et al. | 260/45.8 N |

FOREIGN PATENT DOCUMENTS 407908  5/1974  U.S.S.R. .................................. 546/14

*Primary Examiner*—Morton Foelak
*Assistant Examiner*—R. A. White
*Attorney, Agent, or Firm*—Vincent J. Cavalieri; Luther A. R. Hall

[57] ABSTRACT

4-Siloxy derivatives of sterically hindered piperidines are effective light-stabilizers for plastics. These compounds have at least five alkyl groups in the ring positions 2, 3, 5 and 6 and four alkyl groups in ring positions 2 and 6, preferably methyl and ethyl groups. The ring nitrogen may be unsubstituted or substituted with a monovalent organic residue. The new compounds can be synthesized by O-silylation of 4-hydroxy-polyalkyl-piperidines, preferably by reaction with chlorosilanes.

12 Claims, No Drawings

4-SILOXY DERIVATIVES OF POLYALKYLATED PIPERIDINES

This is a continuation of application Ser. No. 853,664 filed on Nov. 21, 1977 which is a continuation-in-part of application Ser. No. 687,824, filed May 19, 1976, both now abandoned.

This invention relates to new 4-siloxy derivatives of polyalkylated piperidines and their use as stabilizers for organic polymers against photo-deterioration.

In the German laid open patent application No. 2,204,659 there are disclosed compounds of the formula

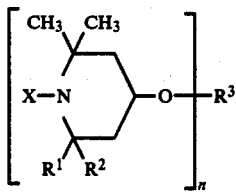

and their use as stabilizers for polymers. Within this general formula inter alia orthosilicates are included represented by the above formula, if n is 4 and $R^3$ is a silicon atom.

Now it has been found that 4-siloxy derivatives of higher alkylated piperidines show an excellent stabilizing action on light-sensitive organic polymers and show certain advantages over the known orthosilicates as for example a higher compatibility with certain polymeric substrates.

The invention therefore relates to new 4-siloxypiperidines of formula I

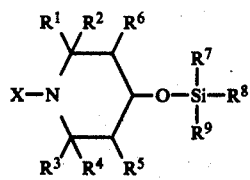

or a mixture of isomers thereof or an acid addition salt thereof, wherein $R^1$ and $R^3$ are each ethyl, $R^2$, $R^4$ and $R^5$ are each methyl, $R^6$ is hydrogen, and $R^5$ and $R^6$ are interchangeable, $R^7$ is hydrogen, methyl, phenyl or vinyl, $R^8$ and $R^9$ are independently of another hydrogen, methyl, phenyl, vinyl, alkoxy having 1-8 C-atoms, phenoxy which may be substituted by an alkyl group having from 1 to 4 carbon atoms, or a residue of the formula

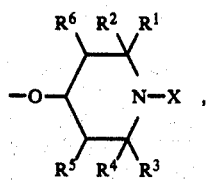

and if $R^7$ and $R^8$ are hydrogen, methyl, phenyl or vinyl, $R^9$ may also be a residue of the formula

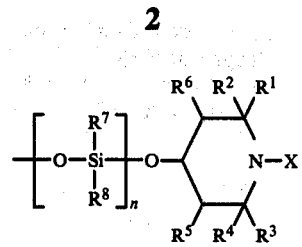

n is an integer from 1 to 10, and

X is hydrogen, alkyl having 1 to 4 carbon atoms, benzyl or an aliphatic acyl group having 1 to 4 carbon atoms, as well as to a composition of matter stabilized against light-induced deterioration, comprising an organic polymer, normally subject to deterioration by light, and from 0.01 to 5.0 percent by weight of a compound of formula I, or a mixture of isomers thereof or an acid addition salt thereof.

When X represents an alkyl group having from 1 to 4 C-atoms, it may be e.g., methyl, ethyl, n-propyl or n-butyl.

When X is an aliphatic acyl group having 1-4 C-atoms, it may be an alkanoic or an alkenoic group and it may be e.g. an acetyl, formyl, propionyl, butyryl, acryloyl or crotonoyl group.

When $R^8$ or $R^9$ are alkoxy having 1-8 C-atoms it may be e.g., a methoxy, ethoxy, isopropoxy, butoxy, hexoxy or octoxy group.

$R^8$ and $R^9$ as phenoxy groups substituted by alkyl having 1 to 4 carbon atoms may be, e.g., toluyloxy, xylyloxy or 4-tert-butylphenoxy.

The 4-siloxypiperidines having the aforementioned general formula I consist of various stereo isomers. Accordingly, by the term "mixture of isomers thereof" are meant mixtures of position isomers at 3- and 5-position and/or various kinds of stereo isomers. At any stage of the synthesis of the compounds according to the invention, the mixture of isomers usually obtained in the preparation of the corresponding 4-piperidinone derivative which is used as starting material, can be separated by methods known per se.

Acid addition salts of compounds of formula I may be for example salts of inorganic acids such as sulfuric, hydrochloric or phosphoric acid; organic carboxylic acids such as formic, acetic, valeric, stearic, oxalic, adipic, sebacic, maleic, benzoic, p-tert. butyl-benzoic, 3,5-ditert.butyl-4-hydroxybenzoic, salicylic or terephthalic acid; sulfonic acids such as methanesulfonic or p-toluenesulfonic acid; or organic phosphorus acids such as diphenyl phosphoric acid or phenyl phosphonic acid.

Preferred are compounds of formula I wherein X is hydrogen, alkyl having 1-4 C-atoms or acetyl, $R^7$ is hydrogen, methyl or phenyl and $R^8$ and $R^9$ are methyl, phenyl or a residue of the formula

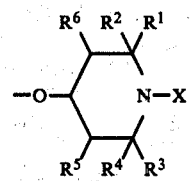

wherein X is hydrogen, alkyl having 1 to 4 carbon atoms or acetyl and $R^1$ to $R^6$ are as defined under formula I.

Most preferred are compounds of formula I
wherein X is hydrogen or methyl,
$R^7$ and $R^8$ are methyl or phenyl, and $R^9$ is methyl, phenyl or a residue of the formula

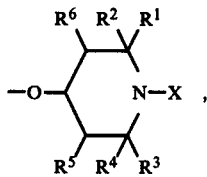

and compounds of formula I
wherein X is hydrogen or methyl,
$R^7$ is methyl or phenyl and
$R^8$ and $R^9$ are methyl, phenyl or a residue of the formula

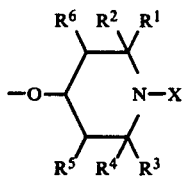

X, in said residues, being hydrogen or methyl while $R^1$ to $R^6$ have the meaning given under formula I.

The following is a list of specific 4-siloxypiperidines of formula I. It is, however, to be understood that the present invention is not limited to these illustrating compounds.

2,6-diethyl-2,3,6-trimethyl-4-trimethylsiloxypiperidine
2,6-diethyl-1,2,3,6-tetramethyl-4-trimethylsiloxypiperidine
2,6-diethyl-2,3,6-trimethyl-4-triphenylsiloxypiperidine
2,6-diethyl-1,2,3,6-tetramethyl-4-triphenylsiloxypiperidine
1-acetyl-2,6-diethyl-2,3,6-trimethyl-4-triphenylsiloxypiperidine
dimethyl-bis-(2,6-diethyl-2,3,6-trimethylpiperidine-4-oxy)-silane
dimethyl-bis-(2,6-diethyl-1,2,3,6-tetramethylpiperidine-4-oxy)-silane
dimethyl-bis-(1-acetyl-2,6-diethyl-2,3,6-trimethylpiperidin-4-oxy)-silane
diphenyl-bis-(2,6-diethyl-2,3,6-trimethylpiperidin-4-oxy)-silane
diphenyl-bis-(2,6-diethyl-1,2,3,6-tetramethylpiperidin-4-oxy)-silane
diphenyl-bis-(1-acetyl-2,6-diethyl-2,3,6-trimethylpiperidin-4-oxy)-silane
methyl-phenyl-bis-(2,6-diethyl-2,3,6-trimethylpiperidin-4-oxy)-silane
methyl-phenyl-bis-(2,6-diethyl-1,2,3,6-tetramethyl-piperidin-4-oxy)-silane
methyl-phenyl-bis-(1-acetyl-2,6-diethyl-2,3,6-trimethyl-piperidin-4-oxy)-silane
methyl-bis-(2,6-diethyl-2,3,6-trimethylpiperidin-4-oxy)-silane
methyl-bis-(2,6-diethyl-1,2,3,6-tetramethylpiperidin-4-oxy)-silane
methyl-bis-(1-acetyl-2,6-diethyl-2,3,6-trimethylpiperidin-4-oxy)-silane
phenyl-bis-(2,6-diethyl-2,3,6-trimethylpiperidin-4-oxy)-silane
phenyl-bis-(2,6-diethyl-1,2,3,6-tetramethylpiperidin-4-oxy)-silane
phenyl-bis-(1-acetyl-2,6-diethyl-2,3,6-trimethylpiperidin-4-oxy)-silane
tri-(2,6-diethyl-2,3,6-trimethylpiperidin-4-oxy)-silane
tri-(2,6-diethyl-1,2,3,6-tetramethylpiperidin-4-oxy)-silane
tri-(1-acetyl-2,6-diethyl-2,3,6-trimethylpiperidin-4-oxy)-silane
methyl-tris-(2,6-diethyl-2,3,6-trimethylpiperidin-4-oxy)-silane
methyl-tris-(2,6-diethyl-1,2,3,6-tetramethylpiperidin-4-oxy)-silane
methyl-tris-(1-acetyl-2,6-diethyl-2,3,6-trimethylpiperidin-4-oxy)-silane
phenyl-tris-(2,6-diethyl-2,3,6-trimethylpiperidin-4-oxy)-silane
phenyl-tris-(2,6-diethyl-1,2,3,6-tetramethylpiperidin-4-oxy)-silane
phenyl-tris-(1-acetyl-2,6-diethyl-2,3,6-trimethylpiperidin-4-oxy)-silane
2,6-diethyl-2,3,6-trimethyl-4-(phenyl-dimethylsiloxy)-piperidine
2,6-diethyl-1,2,3,6-tetramethyl-4-(phenyl-dimethylsiloxy)-piperidine
1-acetyl-2,6-diethyl-2,3,6-trimethyl-4-(phenyl-dimethylsiloxy)-piperidine
1,3-bis-(2,6-diethyl-2,3,6-trimethylpiperidin-4-oxy)-1,1,3,3-tetramethyldisiloxane
1,3-bis-(2,6-diethyl-1,2,3,6-tetramethylpiperidin-4-oxy)-1,1,3,3-tetramethyldisiloxane
1,3-bis-(1-acetyl-2,6-diethyl-2,3,6-trimethylpiperidin-4-oxy)-1,1,3,3-tetramethyldisiloxane
1-benzyl-2,6-diethyl-2,3,6-trimethyl-4-trimethylsiloxypiperidine.

The 4-siloxypiperidines of formula I can be prepared by silylation of the corresponding 4-hydroxy piperidines II $$\begin{array}{c} R^1\ R^2\ R^6 \\ \diagdown\!\!\diagup \\ X\!-\!N\quad\quad\!\!-\!OH \\ \diagup\!\!\diagdown \\ R^3\ R^4\ R^5 \end{array} \quad II$$

with the stoichometric amount of a silane derivative $Y\text{-}Si(R^7)(R^8)(R^9)$ or $(Y)_2Si(R^7)(R^8)$ or $(Y)_3Si(R^7)$ respectively, wherein Y is a group known to be reactive in O-silylation and may be halogen, alkoxy, amino, mono- or dialkylamino or acyloxy, preferably Y is chlorine.

Examples for chlorosilanes usable in this silylation reaction are methyltrichlorosilane, phenyltrichlorosilane, dimethyldichlorosilane, phenyl-methyl-dichlorosilane, diphenyldichlorosilane, trimethylchlorosilane, methyldichlorosilane, phenoxydimethyl-chlorosilane or 1,3-dichloro-1,1,3,3-tetramethyldisiloxane or mixtures of $\omega,\omega'$-dichloropolysiloxanes.

The reaction with chlorosilanes is usually carried out in an inert organic solvent for example in hydrocarbons, e.g., benzene, toluene, cyclohexane or in ethers, e.g., diethylether, dioxane or tetrahydrofuran, and a stoichiometric amount of a base is added. Preferably tertiary amines are used as bases, e.g., triethylamine, tributylamine or diethylaniline.

The tertiary amine may also be used in large excess without using an organic solvent. This method is of particular importance in the silylation of compounds of formula II where X is hydrogen and N-silylation should be avoided.

The 4-hydroxypiperidines of formula II may be prepared by reduction of the corresponding 4-oxopiperidines, for example by catalytic hydrogenation over Raney nickel. The 4-oxopiperidines are accessible on different routes, for example by reaction of ketones, being higher homologues of acetone, with ammonia, as it is described for the preparation of 2,3,6-trimethyl-2,6-diethyl-4-oxopiperidine in Chem.Berichte 41, 777 (1908).

The introduction of the substituent X other than hydrogen may be achieved by substitution of the corresponding NH-compound either in the step of the 4-oxopiperidine or the 4-siloxypiperidine. It is achieved by methods known for the alkylation or acylation of secondary amines, for example by reaction with alkyl halides, with dialkylsulfates, with aldehydes under reductive conditions or with carboxylic acid chlorides or anhydrides.

In accordance with the invention, it has now been discovered that the 4-siloxy-piperidine derivatives of formula I can effectively stabilize a wide range of organic polymers against light-induced deterioration with superior compatibility with polymer substrates. Polymers which can be stabilized in this way include:

1. Polymers which are derived from mono- or diolefines, for example polyethylene which can optionally be crosslinked, polypropylene, polyisobutylene, polymethylbutene-1, polymethylpentene-1, polyisoprene, polybutadiene.

2. Mixtures of the homopolymers cited under (1), for example mixtures of polypropylene and polyethylene, polypropylene and polybutene-1, polypropylene and polyisobutylene.

3. Copolymers of the monomers based on the homopolymers cited under (1), for example ethylene/propylene copolymers, propylene/butene-1 copolymers, propylene/isobutylene copolymers, ethylene/butene-1 copolymers as well as terpolymers of ethylene and propylene with a diene, for example hexadiene, dicyclopentadiene or ethylidene norbornene.

4. Polystyrene.

5. Copolymers of styrene and of α-methylstyrene, for example styrene/butadiene copolymers, styrene/acrylonitrile copolymers, styrene/acrylonitrile/methacrylate copolymers, styrene/acrylonitrile/acrylic ester copolymers, styrene/acrylonitrile copolymers modified with acrylic ester polymers to provide impact strength as well as styrene polymers modified with EPDM to provide impact strength and block-copolymers of styrene.

6. Graft copolymers of styrene, for example the graft polymer of styrene to polybutadiene, the graft polymer of styrene with acrylonitrile to polybutadiene as well as mixtures thereof with the copolymers cited under (5), commonly referred to as acrylonitrile/butadiene/styrene or ABS plastics.

7. Halogen-containing vinyl polymers, for example polyvinyl chloride, polyvinylidene chloride, polyvinyl fluoride, polychloroprene, chlorinated rubbers, vinyl chloride/vinylidene chloride copolymers, vinyl chloride/vinyl acetate copolymers, vinylidene chloride/vinyl acetate copolymers.

8. Polymers which are derived from α,β-unsaturated acids and derivatives thereof, polyacrylates and polymethacrylates, polyacrylic amides and polyacrylonitrile.

9. Polymers which are derived from unsaturated alcohols and amines and from the acyl derivatives thereof or acetals, for example polyvinyl alcohol, polyvinyl acetate, polyvinyl stearate, polyvinyl benzoate, polyvinyl maleate, polyvinyl butyral, polyallyl phthalate, polyallyl melamine and copolymers thereof with other vinyl compounds, for example ethylene/vinyl acetate copolymers.

10. Homopolymers and copolymers which are derived from epoxides, for example polyethylene oxide, polypropyleneoxide or their copolymers with bis-glycidyl ethers.

11. Polyacetals, for example polyoxymethylene, as well as polyoxymethylenes which contain ethylene oxide as comonomer.

12. Polyphenylene oxides.

13. Polyurethanes and polyureas.

14. Polycarbonates.

15. Polysulphones.

16. Polyamides and copolyamides which are derived from diamines and dicarboxylic acids and/or from aminocarboxylic acids or the corresponding lactames, for example polyamide 6, polyamide 6/6, polyamide 6/10, polyamide 11, polyamide 12.

17. Polyesters which are derived from dicarboxylic acids and dialcohols and/or from hydroxycarboxylic acids or the corresponding lactones, for example polyethylene terephthalate, polybutylene terephthalate or poly-1,4-dimethylol-cyclohexane terephthalate.

18. Cross-linked polymers which are derived from aldehydes on the one hand and from phenols, ureas and melamines on the other, for example phenol/formaldehyde, urea/formaldehyde and melamine/formaldehyde resins.

19. Alkyd resins, for example glycerol/phthalic acid resins and mixtures thereof with melamine/formaldehyde resins.

20. Unsaturated polyester resins which are derived from copolyesters of saturated and unsaturated dicarboxylic acids with polyhydric alcohols as well as from vinyl compounds as cross-linking agents.

21. Crosslinked epoxy resins, which are derived from polyepoxides, e.g., from bis-glycidyl ethers or from cycloaliphatic diepoxides.

22. Natural polymers, for example cellulose, rubber, proteins as well as the chemically modified homologous derivatives thereof, for example cellulose acetates, cellulose propionates and cellulose butyrates and the cellulose ethers, for example methyl cellulose.

23. Silicone resins, rubbers and oils.

From these the polymers of groups 1–6, 13 and 16 are of particular interest as the application of the stabilizers has an outstanding effect on these polymers. Particularly preferred polymers are polyolefins, styrene homo- and copolymers, polyurethanes and polyamides.

The stabilizer compounds of formula I are added to the polymers in an amount of from 0.01 to 5% by weight, based on the weight of the polymer. Preferably they are added in an amount of from 0.02 to 1.0 and most preferably from 0.05 to 0.5% by weight.

The stabilizers of formula I may readily be incorporated into the organic polymers by conventional techniques, at any convenient stage prior to the manufacture of shaped articles therefrom. For example, the stabilizer may be mixed with the polymer in dry powder form, or a solution or a suspension of the stabilizer may be mixed with a solution or suspension of the polymer.

The stabilized polymer compositions of the invention may optionally also contain other known stabilizers or other additives usually known in plastics technology, such as the additives listed in British patent specification No. 1 401 924, pages 11 to 13.

Synergistic effects may appear in using such known additives in combination with the stabilizers of formula I. This is especially true with other light-stabilizers and with organic phosphites.

Of particular importance is the combination of the light-stabilizers of formula I with antioxidants, especially for the stabilisation of polyolefins.

The invention is further illustrated by the following Examples in which all parts and percentages are by weight.

EXAMPLES 1-5

39.8 g of 2,6-diethyl-2,3,6-trimethyl-4-hydroxypiperidine and 22 g of triethylamine are dissolved in 600 ml of dioxane. The solution is heated to 60° C. and a solution of 12.9 g of dimethyldichlorosilane in 200 ml of dioxane is added within 90 minutes of this temperature. The reaction is completed by stirring the mixture at 60°-65° C. for 18 hours. After cooling to room-temperature the precipitated triethylamine hydrochloride is filtered off and the filtrate is evaporated under reduced pressure. The oily residue is purified by vacuum distillation yielding dimethyl-bis(2,6-diethyl-2,3,6-trimethylpiperidine-4-oxy)-silane, boiling at 170°-172° C./0.4 mm Hg (Compound No. 1).

According to this procedure 29.9 g of 2,6-diethyl-2,3,6-trimethyl-4-hydroxypiperidine is reacted in dioxane in the presence of 20 g of triethylamine with
(a) 19 g of diphenyldichlorosilane,
(b) 44 g of diphenylchlorosilane,
(c) 16.3 g of trimethylchlorosilane,
(d) 10.6 g of phenyltrichlorosilane, Using the same method of isolation as described above there are obtained
(a) diphenyl-bis(2,6-diethyl-2,3,6-trimethylpiperidine-4-oxy)-silane (Compound No. 2), b.p. 190°-195° C./0.001 mm Hg, viscous syrup.
(b) 2,6-diethyl-2,3-trimethyl-4-(triphenylsiloxy)-piperidine (Compound No. 3), b.p. 135° C./0.005 mm Hg, yellow, viscous mass.
(c) 2,6-diethyl-2,3,6-trimethyl-4-(trimethylsiloxy)-piperidine (Compound No. 4), b.p. 97°-98° C./1.5 mm Hg.
(d) phenyl-tris-(2,6-diethyl-2,3,6-trimethylpiperidine-4-oxy)-silane (Compound No. 5), b.p. 190°-195° C./0.001 mm Hg.

EXAMPLES 6-8

21.1 g of 1,2,3,6-tetramethyl-2,6-diethyl-4-hydroxypiperidine and 20 g of triethylamine are dissolved in 250 ml of dioxane. By addition of 10.9 g of trimethylchlorosilane and using the same procedure of reaction and isolation as described in the previous examples there is obtained 1,2,3,6-tetramethyl-2,6-diethyl-4-(trimethylsiloxy)-piperidine (Compound No. 6), b.p. 78°-79° C./0.35 mm Hg.

According to this procedure, 21.1 g of 1,2,3,6-tetramethyl-2,6-diethyl-4-hydroxypiperidine are reacted in dioxane in the presence of 20 g of triethylamine with
(a) 29.5 g of triphenylchlorisilane,
(b) 12.7 g of diphenyldichlorosilane.

Using the same method of isolation as described above, there are obtained:
(a) 1,2,3,6-tetramethyl-2,6-diethyl-4-(triphenylsiloxy)-piperidine (Compound No. 7), b.p. 135° C./0.005 mm Hg.
(b) diphenyl-bis-(1,2,3,6-tetramethyl-2,6-diethyl-piperidine-4-oxy)-silane (Compound No. 8), b.p. 120°-125° C./0.005 mm Hg.

EXAMPLE 9

A solution of 28.4 g of 3-chloroperbenzoic acid in 200 ml of methylene chloride is dropped into a solution of 16.3 g of 2,6-diethyl-2,3,6-trimethyl-4-(trimethylsiloxy)-piperidine (Compound No. 4) in 50 ml methylene chloride at 25° C. within 2 hours. The reaction mixture rapidly becomes reddish and the forming 3-chlorobenzoic acid is precipitating successively. After a further stirring period of 12 hours the precipitate is filtered off and washed with cold methylene chloride. The filtrate is washed with 2 n sodium hydroxide solution and with water. The methylene chloride solution is dried over $Na_2SO_4$ and evaporated to dryness. The oily residue is purified by high-vacuum distillation yielding 2,6-diethyl-2,3,6-trimethyl-4-(trimethylsiloxy)-piperidine-1-oxy (Compound No. 9) b.p. 107°-111° C./0.06 mm Hg.

EXAMPLE 10

100 parts of polypropylene powder (Moplen, fibre grade, Montedison Comp.) and 0.2 parts octadecyl β-(3,5-di-tert. butyl-4-hydroxyphenyl)-propionate as antioxidant and 0.25 parts of a light-stabilizer listed in Table 1 are homogenised in a Brabender plastograph during 10 minutes at 200° C. The resulting mass is pressed to a 2 to 3 mm thick sheet in a laboratory press. The sheet is hot pressed in a hydraulic press during 6 minutes at 260° C. and a pressure of 12 tons yielding a 0.5 mm thick film which is quenched immediately in cold water. By the same procedure a 0.1 mm film is made from the 0.5 mm film.

Test specimens of 66 ×44 mm are cut from the film and irradiated in a "Xenotest 150" radiation equipment. The content of carbonyl groups of the irradiated films is periodically controlled by infrared spectroscopy. The increase of carbonyl groups characterised by the infrared extinction at 5.85μ is a relevant measure for the light-induced deterioration of polypropylene (see L. Balaban et al., J.Polymer Sci., Part C, 22 (1969) 1059-1071) and is, according to experience, accompanied by a gradual loss of the mechanical properties of the polymer. Thus the film is completely brittle when the carbonyl extinction becomes 0.30. The protective action of the different light-stabilizers of the invention is shown in Table I.

Table 1

| Compound (No. given in Examples 1-6) | Irradiation time (hours) | CO extinction (5.85 μ) |
| --- | --- | --- |
| none | 1050 | 0.30 |
| No. 1 | 7300 | 0.08 |
| 2 | 7300 | 0.07 |
| 3 | >7300 | 0.04 |

What we claim is:
1. A compound of formula I

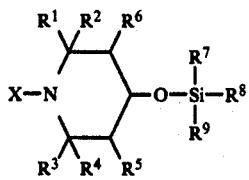 (I)

or a mixture of isomers thereof or an acid addition salt thereof, wherein $R^1$ and $R^3$ are each ethyl, $R^2$, $R^4$ and $R^5$ are each methyl, $R^6$ is hydrogen and $R^5$ and $R^6$ are interchangeable, $R^7$ is hydrogen, methyl, phenyl or vinyl, $R^8$ and $R^9$ are independently of each other hydrogen, methyl, phenyl, vinyl, alkoxy having 1–8 C-atoms, phenoxy which may be substituted by an alkyl group having from 1 to 4 carbon atoms, or a group of the formula

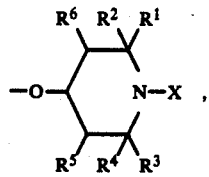

and if $R^7$ and $R^8$ are hydrogen, methyl, phenyl or vinyl, $R^9$ may also be a residue of the formula

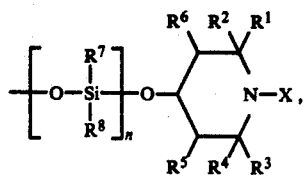

n is an integer from 1 to 10, and

X is hydrogen, alkyl having 1 to 4 C-atoms, benzyl or an aliphatic acyl group having 1 to 4 C-atoms.

2. A compound according to claim 1 of formula I, wherein X is hydrogen, alkyl having 1–4 C-atoms or acetyl, $R^7$ is hydrogen, methyl or phenyl and $R^8$ and $R^9$ are methyl, phenyl or a group of the formula

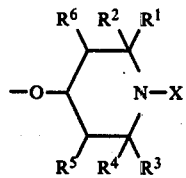

wherein X is hydrogen, alkyl having 1 to 4 C-atoms or acetyl, and $R^1$ to $R^6$ are as defined in claim 1.

3. A compound according to claim 1 of formula I, wherein X is hydrogen or methyl, $R^7$ and $R^8$ are methyl or phenyl and $R^9$ is methyl, phenyl or a residue of the formula

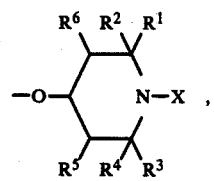

wherein X is hydrogen or methyl, and $R^1$ to $R^6$ are as defined in claim 1.

4. A compound according to claim 1 of formula I wherein X is hydrogen or methyl, $R^7$ is methyl or phenyl and $R^8$ and $R^9$ are methyl, phenyl or a group of the formula

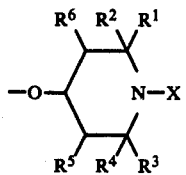

wherein X is hydrogen or methyl, and $R^1$ to $R^6$ are as defined in claim 1.

5. A composition of matter stabilized against light-induced deterioration comprising an organic polymer, normally subject to deterioration by light, and from 0.01 to 5.0 percent by weight of a compound of formula I, or a mixture of isomers thereof or an acid addition salt thereof, as claimed in claim 1.

6. A composition according to claim 5, wherein the organic polymer is a polyolefin or a styrene homo- or copolymer.

7. A composition according to claim 5, wherein the organic polymer is a polyurethane or polyamide.

8. The compound according to claim 1, dimethyl-bis-(2,6-diethyl-2,3,6-trimethylpiperidine-4-oxy)-silane.

9. The compound according to claim 1, diphenyl-bis-(2,6-diethyl-2,3,6-trimethylpiperidine-4-oxy)-silane.

10. The compound according to claim 1, 2,6-diethyl-2,3,6-trimethyl-4-(triphenylsiloxy)-piperidine.

11. The compound according to claim 1, phenyl-tris-(2,6-diethyl-2,3,6-trimethylpiperidine-4-oxy)-silane.

12. The compound according to claim 1, 1,2,3,6-tetramethyl-2,6-diethyl-4-(trimethylsiloxy)-piperidine.

* * * * *